United States Patent
Veca et al.

(10) Patent No.: US 10,005,390 B2
(45) Date of Patent: Jun. 26, 2018

(54) MOTOR-VEHICLE PASSENGER-COMPARTMENT COMPONENT, AND A METHOD FOR MANUFACTURING THIS COMPONENT

(71) Applicant: C.R.F. Società Consortile per Azioni, Orbassano (Turin) (IT)

(72) Inventors: Antonino Domenico Veca, Casalborgone (IT); Matteo Strumia, Carmagnola (IT); Vito Guido Lambertini, Giaveno (IT); Maurizio Servetti, Chieri (IT)

(73) Assignee: C.R.F. SOCIETÀ CONSORTILE PER AZIONI, Orbassano (Turin) (IT)

( * ) Notice: Subject to any disclaimer, the term of this patent is extended or adjusted under 35 U.S.C. 154(b) by 0 days. days.

(21) Appl. No.: 15/674,244

(22) Filed: Aug. 10, 2017

(65) Prior Publication Data
US 2018/0147982 A1    May 31, 2018

(30) Foreign Application Priority Data
Nov. 28, 2016    (EP) .................................... 16200846

(51) Int. Cl.
*B60Q 1/00*    (2006.01)
*B60Q 9/00*    (2006.01)
(Continued)

(52) U.S. Cl.
CPC ............ *B60Q 9/00* (2013.01); *B29C 35/0805* (2013.01); *B29C 44/12* (2013.01);
(Continued)

(58) Field of Classification Search
None
See application file for complete search history.

(56) References Cited

U.S. PATENT DOCUMENTS 5,952,630 A    9/1999    Filion et al.
7,954,874 B2    6/2011    Ohlinger et al.
(Continued)

FOREIGN PATENT DOCUMENTS

EP    3124197 A1    2/2017
WO    2012055934 A1    5/2012

OTHER PUBLICATIONS

European Search Report for EP Application No. 16200846 dated May 16, 2017, 3 pages.

*Primary Examiner* — Thomas McCormack
(74) *Attorney, Agent, or Firm* — Heslin Rothenberg Farley & Mesiti P.C.; Victor A. Cardona, Esq.

(57) ABSTRACT

A component for the passenger compartment of a motor vehicle includes a rigid supporting body, made of plastic material, an outer upholstery skin, made of plastic material, and a padding body made of foamed plastic material, which is set between the rigid body and the outer upholstery skin. The rigid body and the outer skin have portions formed by a polymeric material with carbon-based nanofillers, which have respective inner surfaces facing the padding body, which include one or more paths where said polymeric material with carbon-based nanofillers has been rendered electrically conductive by laser irradiation to define one or more electrical circuits, and one or more piezoresistive areas where the polymeric material has been rendered piezoresistive by laser irradiation to define one or more electrical switches, which can be activated by exerting a localized pressure on the outer upholstery skin.

5 Claims, 2 Drawing Sheets

(51) Int. Cl.

| | |
|---|---|
| *B60R 16/00* | (2006.01) |
| *G08B 21/18* | (2006.01) |
| *B29C 45/14* | (2006.01) |
| *B29C 44/12* | (2006.01) |
| *B29C 35/08* | (2006.01) |
| *G01N 27/04* | (2006.01) |
| *B60R 13/02* | (2006.01) |
| *B60N 2/46* | (2006.01) |
| *B29K 105/04* | (2006.01) |
| *B29K 105/16* | (2006.01) |
| *B29K 507/04* | (2006.01) |
| *B29L 31/30* | (2006.01) |
| *H03K 17/96* | (2006.01) |
| *B60N 2/75* | (2018.01) |

(52) U.S. Cl.
CPC ...... *B29C 45/14065* (2013.01); *B60R 16/005* (2013.01); *G01N 27/041* (2013.01); *G08B 21/182* (2013.01); *B29C 2035/0838* (2013.01); *B29K 2105/04* (2013.01); *B29K 2105/16* (2013.01); *B29K 2507/04* (2013.01); *B29K 2995/0005* (2013.01); *B29L 2031/3014* (2013.01); *B29L 2031/3026* (2013.01); *B60N 2/4693* (2013.01); *B60N 2/797* (2018.02); *B60R 13/0243* (2013.01); *B60R 13/0256* (2013.01); *B60R 2013/0287* (2013.01); *H03K 17/964* (2013.01); *H03K 17/9645* (2013.01)

(56) References Cited

U.S. PATENT DOCUMENTS

2007/0151835 A1    7/2007   Rakers et al.
2007/0235297 A1   10/2007   Stoschek et al.

MOTOR-VEHICLE PASSENGER-COMPARTMENT COMPONENT, AND A METHOD FOR MANUFACTURING THIS COMPONENT

CROSS REFERENCE TO RELATED APPLICATIONS

This application claims priority to European Application No. EP16200846.0 filed on Nov. 28, 2016. The entire disclosure of the prior application is hereby incorporated herein by reference.

FIELD OF THE INVENTION

The present invention relates to components for the passenger compartment of a motor vehicle, in particular to motor-vehicle dashboards or other components of the passenger compartment, such as internal door panels, armrests, or the like.

The invention regards in particular a component for the passenger compartment of a motor vehicle of the type comprising:
  a rigid supporting body, made of plastic material;
  an outer upholstery skin, made of plastic material; and
  a padding body made of foamed plastic material, which is set between the rigid body and the outer skin and is sufficiently flexible to enable a user to cause a local deformation thereof by exerting a localized pressure on the outer skin.

PRIOR ART

Components of the type specified above present the advantage of reproducing the same visual appearance and sensation to the touch as those of high-quality components, with upholstery in natural or synthetic leather, at the same time guaranteeing relatively low production costs. In more conventional solutions, the above components are provided with openings and seats designed to receive pushbuttons for operating various components of the motor vehicle and the corresponding wiring. There have on the other hand already been proposed in the past solutions for motor-vehicle dashboards or similar components in which elements of the electrical circuit associated to the dashboard, such as electrical switches, sensors, and the corresponding electrical connections, are integrated in the component. An example of solution of this type is illustrated in the document U.S. Pat. No. 7,954,874 B2. Another solution of this type is described in the European patent application EP 15179375 filed in the name of the present applicant, which forms part of the prior art as per Art. 54(3) EPC.

A component of the type indicated in the preamble of claim 1 is known from U.S. Pat. No. 5,952,630 A.

The present applicant has proposed in the document WO 2012/055934 A1 a method for producing conductive and/or piezoresistive tracks in a non-conductive polymeric substrate via laser irradiation, where the substrate is a composite polymeric material, comprising a matrix including a non-char-forming polymer, i.e., a polymer that is not liable to charring following upon thermal degradation, and a dispersed phase comprising carbon or carbon-nitride nanotubes or carbon nanofibers.

The present invention stems from the desire to find an advantageous application of the above method for the production of components for the passenger compartment of a motor vehicle such as dashboards, internal door panels, armrests, or the like.

OBJECT OF THE INVENTION

An object of the present invention is consequently to provide a component for the passenger compartment of a motor vehicle of the type indicated at the start of the present description that will exploit in an advantageous way the possibilities offered by the method proposed by the present applicant in the document WO 2012/055934 A1.

A further object of the invention is to achieve the aforesaid aim through a component that, on the one hand, will be simple and inexpensive to produce and, on the other hand, will present altogether innovative aesthetic and tactile characteristics and will be such as to be extremely functional, convenient to use, and with an attractive appearance for the user.

Yet a further object of the invention is to provide a component of the type specified above, in which there can be easily integrated further innovative functions, including that of monitoring ageing of the plastic material constituting the outer skin, to verify the suitability of the component to function properly in the case of explosion of an airbag associated thereto.

SUMMARY OF THE INVENTION

With a view to achieving the aforesaid purposes, the subject of the present invention is a component for the passenger compartment of a motor vehicle that presents the characteristics of claim 1.

In a first embodiment, the electrical circuits defined on the inner surfaces of the rigid body and of the outer skin are connected together by means of auxiliary electrical conductors, for example associated to portions of the rigid body of the component that directly face the outer upholstery skin, without interposition of the padding body made of foamed plastic material.

In an alternative and particularly preferred embodiment, the electrical circuits defined on the inner surfaces of the rigid body and of the outer skin are connected together in wireless mode, these electrical circuits including at least one coiled path functioning as receiving and transmitting antenna on each of the inner surfaces of the rigid body and of the outer skin.

In a further embodiment, the above component moreover comprises an electronic control unit for control of the aforesaid electrical circuits, the electronic control unit being configured for monitoring the electrical resistance of one or more of the aforesaid electrically conductive paths formed on the inner surface of the outer upholstery skin and for generating an alarm signal when the electrical resistance measured departs from a predetermined value, corresponding to a maximum acceptable value of the hardness of the outer upholstery skin, there being a direct correlation between the value of hardness of the outer skin and the electrical resistance associated to the area itself.

The above further function is particularly desired, in so far as the experiments conducted by the present applicant have shown that hardening due to ageing of the outer skin can generate the projection of fragments of plastic material following upon explosion of an airbag, with consequent harm to the occupants of the passenger compartment of the motor vehicle.

DETAILED DESCRIPTION OF EMBODIMENTS OF THE INVENTION

Further characteristics and advantages of the invention will emerge from the ensuing description with reference to the annexed drawings, which are provided purely by way of non-limiting example and in which.

Figure 1:
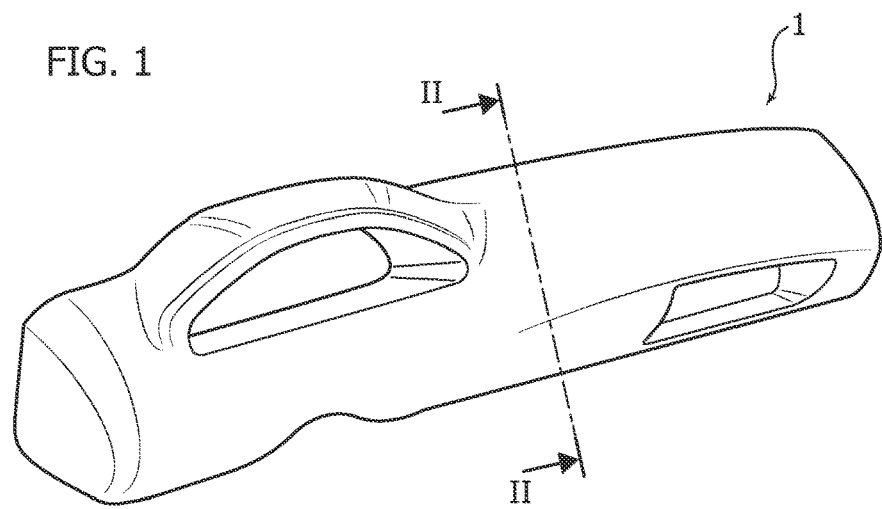
FIG. 1 is a schematic perspective view of a motor-vehicle dashboard according to the present invention.
Figure 2:
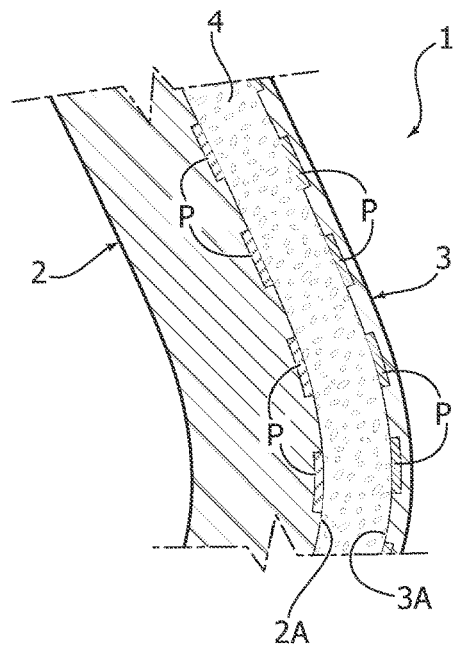
FIG. 2 is a detail at an enlarged scale of a cross-sectional view according to the line II-II of FIG. 1.
Figure 2A:
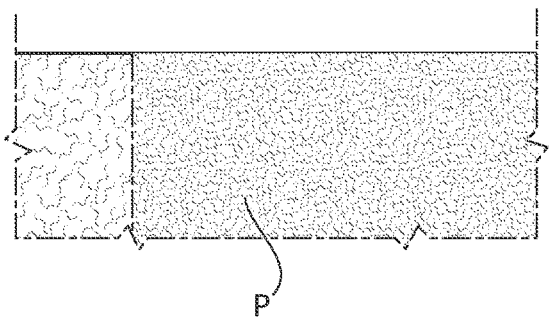
FIG. 2A illustrates at an enlarged scale a detail of FIG. 2.

In FIG. 1, the reference number 1 designates as a whole a motor-vehicle dashboard. With reference to FIG. 2, the dashboard 1 comprises a rigid supporting body 2 made of plastic material, for example polypropylene. Applied over the rigid body 2 is an outer upholstery skin 3, with interposition of a padding body 4 made of foamed plastic material, for example foamed polyurethane. The outer upholstery skin 3 is made, for example, of polyvinylchloride (PVC), or thermoplastic olefin (TPO), or polyurethane (PU).

According to a technique in itself conventional, the dashboard 1 is obtained by setting the rigid body 2 and the outer upholstery skin 3 within a mold, in positions at a distance apart, and injecting in the gap comprised between the elements 2, 3, for example, an expandable bicomponent resin, which cross-links in such a way as to form the body 4 of the padding.

According to an important characteristic of the present invention, both the rigid body 2 and the outer upholstery skin 3 have respective functionalized portions constituted by a polymeric material with carbon-based nanofillers, according to the teachings of the document WO 2012/055934 A1 filed in the name of the present applicant. In the process known from the above document, a basic polymeric material is added with carbon-based nanofillers, for example carbon or carbon-nitride nanotubes or carbon nanofibers in an amount insufficient to render the material electrically conductive. Each of the two bodies 2, 3 is subjected to the process known from WO 2012/055934 A1, which envisages directing a laser beam L emitted by a laser head H (FIG. 3) on the substrate of polymeric material in order to render the substrate electrically conductive along one or more paths P where the laser beam causes charring of the material.

Figure 3:
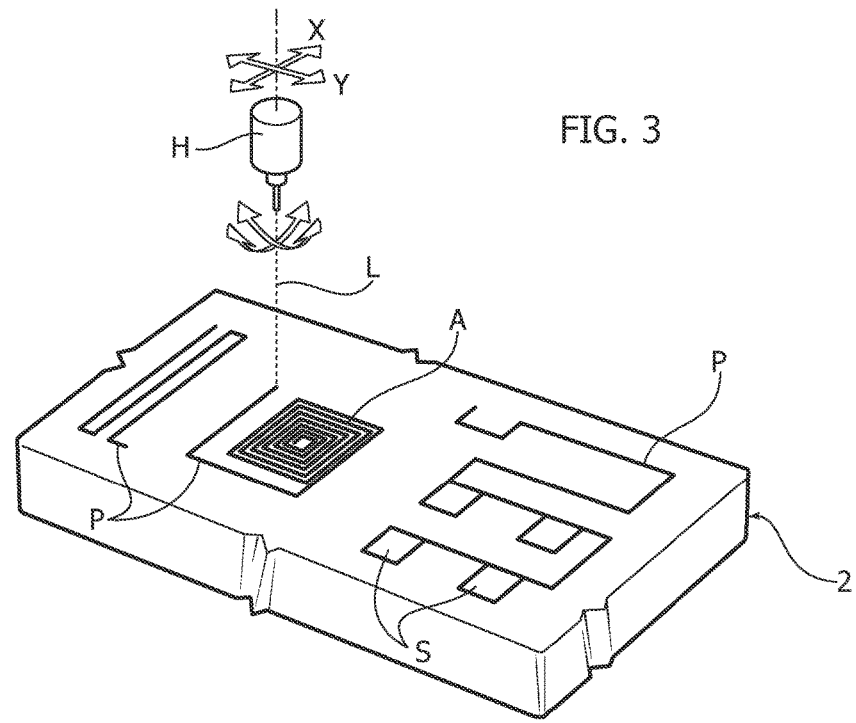
FIG. 3 is a schematic view that illustrates a step of the method according to the invention.

FIG. 3 shows schematically a laser head H, which can be moved in two orthogonal directions X, Y and is moreover equipped with means for causing oscillation of the laser beam L in a plane or in two mutually orthogonal planes. The solution schematically illustrated in FIG. 3 is provided purely by way of example, it being possible to envisage that it is, instead, the substrate that moves with respect to the laser head or envisage a combination of movements of the substrate and of the laser head. The details regarding the basic material, the type of nanofillers, and the type of laser that can be used are not illustrated herein, for greater simplicity and clarity, given that these details, taken in themselves, do not fall within the scope of the present invention and can be obtained in any known way, according to the teachings contained in the document WO 2012/055934 A1.

According to the present invention, laser irradiation that brings about charring of the material along predetermined paths P is carried out on the inner surfaces 2A, 3A of the rigid body 2 and of the outer upholstery skin 3, before these elements are set in the mold for injection of the resin that is to constitute the padding body 4 of foamed plastic material.

The electrically conductive paths P formed on the inner surfaces 2A, 3A facing the padding body 4 define one or more electrical circuits. The electrical circuits formed on the two surfaces 2A, 3A are moreover connected together.

In a first embodiment (see FIG. 4), this connection is carried out by means of electrical conductors C associated, for example, to areas of the dashboard 1 in which the outer skin 3 is adjacent to the rigid body 2, without portions of the body 4 set in between.

Figure 4:
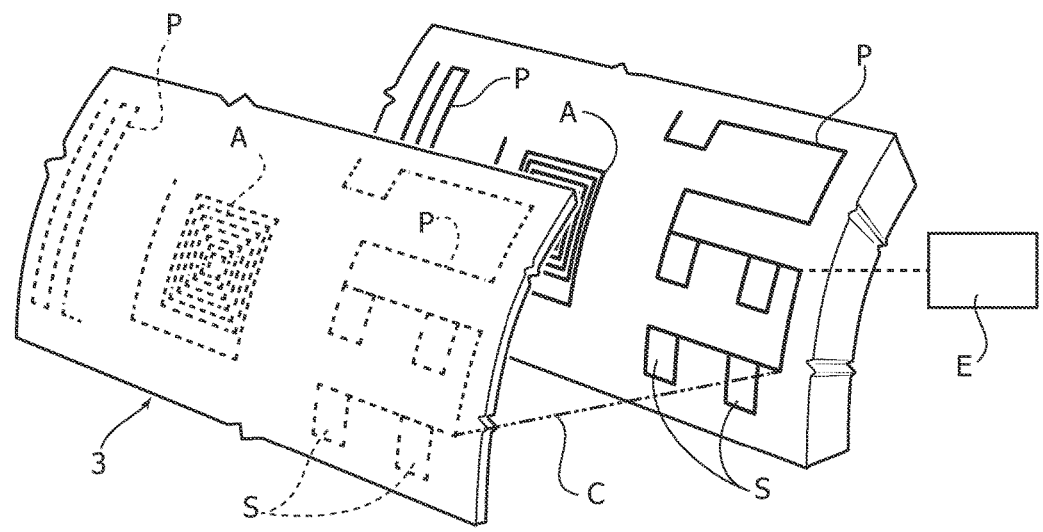
FIG. 4 is an exploded and schematic perspective view of the rigid support and of the outer skin of the dashboard of FIG. 1, with the padding of foamed plastic material removed for greater clarity.

In an alternative and preferred embodiment, instead, which is also illustrated in FIGS. 3 and 4, the electrical circuits formed on the inner surfaces 2A, 3A are connected together in wireless mode. For this purpose, formed on each of the surfaces 2A, 3A is an electrically conductive coiled path A, which defines a transmitting and receiving antenna for wireless connection to a corresponding antenna A prearranged on the other of the two surfaces 2A, 3A.

According to a further characteristic of the invention, laser irradiation on each of the inner surfaces 2A, 3A is carried out so as to form piezoresistive areas S (FIGS. 3 and 4) connected to electrically conductive lines P. The piezoresistive areas S define one or more electrical switches that can be activated by exerting a localized pressure on the outer skin 3 of the final component obtained. In this way, the areas selected S formed on the inner surface of the upholstery skin 3 function as pushbuttons for operating various components of the motor vehicle. The pressure exerted on the areas S generates an electrical signal that is transmitted, in wireless mode or via electrical conductors, to the circuit provided on the rigid support 2 and from this to an electronic control unit E (illustrated schematically in FIG. 4), which activates accordingly the corresponding functions in the motor vehicle.

In a particularly advantageous embodiment, the electronic control unit E is configured for monitoring periodically the electrical resistance of selected portions of the electrical circuit defined by the electrically conductive paths P formed on the inner surface of the outer upholstery skin 3. Experiments conducted by the present applicant have shown that in this way it is possible to monitor the hardness of the outer upholstery skin 3. The electrical resistivity, and consequently the electrical resistance of the skin 3, varies with the hardness of the material. The experiments show that ageing of the plastic material constituting the outer upholstery skin gives rise to hardening. The electronic control unit E may, for example, be programmed for supplying periodically an electric current through electrically conductive paths P distributed over the inner surface of the outer skin 3, and for consequently measuring the electrical resistance. The electronic control unit can be programmed for generating an alarm signal in the case where the electrical resistance measured departs from a predetermined value, indicating unacceptable hardness of the material. An excessive hardness of the outer upholstery skin may cause in fact harm to the occupants of the passenger compartment of the motor vehicle in the case of explosion of an airbag associated to the motor-vehicle dashboard, on account of the fragments of plastic material deriving from shattering of the outer skin. With the system described above, it is thus possible to provide in a simple and efficient way monitoring of ageing of the material constituting the outer skin so as to generate an alarm signal in the case of excessive deterioration.

Of course, without prejudice to the principle of the invention, the details of construction and the embodiments may vary widely with respect to what is described and illustrated herein purely by way of example, without thereby departing from the scope of the present invention.

What is claimed is:

1. A component for the passenger compartment of a motor vehicle comprising:
   a rigid supporting body, made of plastic material;
   an outer upholstery skin, made of plastic material; and
   a padding body made of foamed plastic material, which is set between the rigid body and the outer upholstery skin and is sufficiently flexible as to enable a user of cause a local deformation thereof by exerting a localized pressure on the outer upholstery skin,
   wherein said passenger-compartment component is provided with one or more electrical switches that can be activated by exerting a localized pressure on the outer upholstery skin,
   said rigid body and said outer skin having respective portions comprising a polymeric material with carbon-based nanofillers;
   said portions of the rigid body and of the outer upholstery skin having respective inner surfaces facing said padding body,
   said inner surfaces including one or more functionalized piezoresistive areas where said polymeric material with carbon-based nanofillers has been rendered piezoresistive locally by laser irradiation, so as to define said one or more electrical switches,
   said inner surfaces including one or more functionalized paths where said polymeric material with carbon-based nanofillers has been rendered electrically conductive locally by laser irradiation so as to define one or more electrical circuits distinct from non-conductive areas to which said piezoresistive areas are electrically connected,
   the electrical circuits thus defined on the inner surfaces of the rigid body and of the outer skin being electrically connected together,
   wherein the electrical circuits defined on the inner surfaces of the rigid body and of the outer upholstery skin are connected together in wireless mode, said electrical circuits defined on each of said inner surfaces including at least one coiled path functioning as receiving and transmitting antenna.

2. The component according to claim 1, wherein the electrical circuits defined on the inner surfaces of the rigid body and of the outer upholstery skin are connected together by means of additional electrical conductors.

3. The component according to claim 1, further comprising an electronic control unit for control of said electrical circuits, said electronic control unit being configured for monitoring the electrical resistance of one or more of the aforesaid electrically conductive paths formed on the inner surface of said outer upholstery skin and for generating an alarm signal when the electrical resistance measured departs from a predetermined value, corresponding to a maximum acceptable value of the hardness of the outer upholstery skin.

4. A method for producing a component for the passenger compartment of a motor vehicle according to claim 1, wherein each of said rigid body and said outer upholstery skin is obtained starting from a polymeric material with carbon-based nanofillers, wherein said rigid body and said outer upholstery skin are pre-arranged within a mold in positions at a distance apart, for injection between them of a plastic resin designed to constitute said padding body made of foamed plastic material, wherein before setting said rigid body and said outer upholstery skin in the mold, the inner surfaces of said rigid body and of said outer upholstery skin designed to face the padding body of foamed plastic material are subjected to laser irradiation so as to render the polymeric material with carbon-based nanofillers that constitutes said elements electrically conductive in one or more paths that define one or more electrical circuits, and so as to render one or more selected areas of said inner surfaces piezoresistive so as to define one or more electrical switches that can be activated by exerting a localized pressure on the outer upholstery skin.

5. A method for monitoring the hardness of the outer upholstery skin of a component for the passenger compartment of a motor vehicle according to claim 3, wherein selected electrically conductive paths formed on the inner surface of the outer upholstery skin are supplied with electric current, wherein the electrical resistance of said electrically conductive paths is consequently determined, and wherein an alarm signal is generated when the electrical resistance measured departs from a predetermined value.

* * * * *